United States Patent [19]

Singh

[11] Patent Number: 5,663,387

[45] Date of Patent: Sep. 2, 1997

[54] LIPOSOMES CONTAINING POLYMERIZED LIPIDS FOR NON-COVALENT IMMOBILIZATION OF PROTEINS AND ENZYMES

[75] Inventor: Alok Singh, Spring Field, Va.

[73] Assignee: The United States of America as represented by the Secretary of the Navy, Washington, D.C.

[21] Appl. No.: 512,355

[22] Filed: Aug. 8, 1995

Related U.S. Application Data

[62] Division of Ser. No. 220,124, Mar. 30, 1994, Pat. No. 5,466,467.
[51] Int. Cl.$^6$ .................................. C07F 9/02; C07F 9/10
[52] U.S. Cl. ............................ 554/80; 554/81; 424/450
[58] Field of Search ..................... 424/450; 554/80, 554/81

[56] References Cited

U.S. PATENT DOCUMENTS

| | | | |
|---|---|---|---|
| 4,867,917 | 9/1989 | Schnur et al. | 260/413 |
| 4,913,902 | 4/1990 | Kilpatrick et al. | 424/85.8 |
| 5,258,499 | 11/1993 | Konigsberg et al. | 530/351 |
| 5,290,960 | 3/1994 | Singh | 554/79 |

OTHER PUBLICATIONS

Abstracts, The American Chemical Society 205th National Meeting, Denver, Colorado, Mar. 28 – Apr. 2, 1993.
Letter from Nancy B. Jackson to A. J. Pathak dated 9 Mar. 1995.
Singh, A., and Schnur, J.M., Chapter 7–Polymerizable Phospholipids in Phospholipids Handbook, Gregor Cevc (Editor), Marcell Dekker, Inc., New York, pp. 233–291 (1993).
Ringsdorf, H., Schlarb, B., Venzmer, J., 27 Angew. Chem. Int. Ed. Engl. pp. 113 (1988).
Regen, S.L., Krizenstejn, P., Singh, A., 16 Macromolecules p. 335 (1983).

Markowitz, M., Schnur, J., and Singh, A., *The influence of the polar headgroups of acidic diacetylenic phospholipids on tubule formation, microstructure morphology and Langmuir film behavior*, 62 Chemistry and Physics of Lipids, pp. 193–204 (1992).
Markowitz, M., Baral, S., Brandow, S., and Singh, A., *Palladium ion assisted formation and metallization of lipid tubules*, 224 Thin Solid Films pp. 242–247 (1993).
Wasserman et al., *High–Yield Method for Immobilization of Enzymes*, 22 Biotechnology and Bioengineering pp. 271–287 (1980).
Epton et al., *A Study of Carbonic Anhydrase Covalently Bound to a Poly(acryloylmorpholine) Network in Aqueous/ Organic Solvents*, 5(1) Biochemical Society Transactions pp. 274–276 (1977).

(List continued on next page.)

Primary Examiner—Gollamudi S. Kishore
Attorney, Agent, or Firm—Thomas E. McDonnell; Ralph T. Webb

[57] ABSTRACT

The lipids of this invention are derivatives of phosphatidyl choline having the general chemical formula:

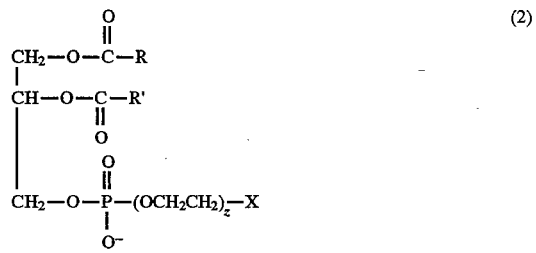

wherein at least one of R and R' is a polymerizable unsaturated alkyl group, acid or ester, wherein X includes an iminodiacetic acid in the polymerizable metal chelating lipid (2) and wherein z is an integer from 1–20 including 1 and 20. Lipid microstructures are formed by mixing the polymerizable metal chelating lipid monomers (2) with polymerizable non-chelating lipid monomers wherein X includes a non-chelating group, for example, —$N^+(CH_3)_3$.

12 Claims, 2 Drawing Sheets

OTHER PUBLICATIONS

Crumbliss et al., *Preparation and Activity of Carbonic Anhydrase Immobilized on Porous Silica Beads and Graphite Rods*, 31 Biotechnology and Bioengineering pp. 796–801 (1988).

Cantenys et al., *Covalent Attachment of Insulin to the Outer Surface of Liposomes*, 117 (2) Biochemical and Biophysical Research Communications, pp. 399–405 (Dec. 16, 1983).

Martin et al., *Irreversible Coupling of Immunoglobulin Fragments to Performed Vesicles*, 257(1) The Journal of Biological Chemistry pp. 286–288 (Jan. 10, 1982).

O'Daly et al., *Activity of Carbonic Anhydrase Immobilized on Porous Silica Beads in Organic Media*, 12 Biotechnology and Applied Biochemistry, pp. 11–19 (1990).

Wulf G., Polymeric Reagents and Catalysis, Ford, W. (Editor), ACS Symposium Series 308, American Chemical Society, pp. 186–230, Washington, DC (1986).

Sinha, P. et al., 28A Ind. J. Chem. p. 33515 (1989).

R.L. Juliano, S.L. Regen, M. Singh, M.J. Hsu and A. Singh, *Stability properties of photopolymerized liposomes*, 1 Biotechnology pp. 882–885 (1983).

Singh, A., *An efficient synthesis of phosphatidylcholines*, 31 Journal of Lipid Research, pp. 1522–1525 (1990).

S.L. Regen, A. Singh, G. Oehme, and M. Singh, *Polymerized phosphatidylcholine vesicles: Synthesis and characterization* J. Amer. Chem. Soc. 104:791–795 (1982).

LIPOSOMES CONTAINING POLYMERIZED LIPIDS FOR NON-COVALENT IMMOBILIZATION OF PROTEINS AND ENZYMES

CROSS REFERENCE TO RELATED APPLICATION

This application is a divisional application of parent application (pursuant to 37 CFR § 1.60) having Ser. No. 08/220,124 filed on 30 Mar. 1994, now U.S. Pat. No. 5,466,467 and entitled, LIPOSOMES CONTAINING POLYMERIZED LIPIDS FOR NON-COVALENT IMMOBILIZATION OF PROTEINS AND ENZYMES (AS AMENDED).

BACKGROUND OF THE INVENTION

1. Field of the Invention

The presently claimed invention relates to the use of polymerizable lipid amphiphiles in the immobilization of proteins and enzymes onto lipid polymers by non-covalent hydrogen bonding (i.e., electrostatic forces). More particularly, the presently claimed invention relates to the synthesis of polymerizable lipids and the formation of lipid vesicles (e.g. liposomes) used to immobilize enzymes and proteins via a metal ion bridge. The metal ion is chelated to functionalities on both the lipid vesicles and to amino acid residues of proteins or enzymes.

2. Description of the Related Art

Polymerizable phospholipids have been used in the stabilization of molecular assemblies and in the development of strategies to expand the usefulness of the lipid assemblies. See Singh, A., Schnur, J. M., POLYMERIZABLE PHOSPHOLIPIDS IN PHOSPHOLIPID HANDBOOK, Cevc, C., Ed., Marcel Dekker Inc., N.Y. pp. 233–287 (1993). See Ringsdorf, H., Schlarb, B., Venzmer, J., 27 ANGEW. CHEM. INT. ED. ENGL. pp. 113 (1988). These strategies include alteration of surface properties of polymer films and construction of a polymerized lipid-membrane surface equipped with reactive sites suitable for chemical interactions, See Regen, S. L., Kirzenstejn, P., Singh, A., 16 MACROMOLECULES pp. 335 (1983) incorporated herein by reference in its entirety and for all purposes. See Markowitz, M. A., Schnur, J. M. and Singh, A., 62 CHEM. PHYS. LIPIDS pp. 193 (1992). See Markowitz, M. A., Baral, S., Brandow, S., and Singh, A., 224 THIN SOLID FILMS pp. 242 (1983). U.S. Pat. No. 5,258,499 (Konigsberg et al.) discloses the use of a liposome. In the Konigsberg et al. patent, the invention includes a composition of matter comprising a liposome which is covalently bound to a ligand, for example, a protein or an enzyme. (Column 2, lines 40–47). The ligands are covalently attached to the liposome surface by coupling agents which are covalently bonded to the ligand. (Column 4, lines 1–5). U.S. Pat. No. 4,913,902 (Kilpatrick et al.) discloses the use of liposomes as well. Liposomes are used to bind various ligands that exist in solution. Thereafter, the liposome-ligand(s) are extracted from solution by filtration. In this manner, the various ligands are extracted from solution by the use of the claimed liposomes of Kilpatrick et al. At column 3, lines 66–68 and column 4, lines 1–5, it is stated that > These ligands may be covalently bound to phospholipids used to form liposomes by conventional techniques, either by attracting the ligand to preformed liposomes or by binding the ligand to a phospholipid and incorporating the resulting amphiphilic molecules into liposomes during formation thereof.

At column 3, lines 9–14 and lines 34–36 it is further stated that

> Ligands which will bind to any of a variety of target molecules can be bound to liposomes to practice the present invention. Exemplary of such ligands, and the target molecules bound thereby, are the following: . . . Chelating Agents and Metal Ions . . .

The Kilpatrick et al. patent discloses the use of a ligand which may be covalently bound to the liposome to remove a target molecule. The covalently bound ligand, for example, a chelating agent, may be used to remove a target molecule, for example, a metal ion.

Various other papers disclose the covalent binding of ligands to liposomes or to other materials, such as glass microbeads or polymers. See Wasserman et al., *High-Yield Method for Immobilization of Enzymes*, 22 BIOTECHNOLOGY AND BIOENGINEERING pp. 271–287 (1980); Epton et al., *A Study of Carbonic Anhydrase Covalently Bound to a Poly (acryloylmorpoline) Network in Aqueous/Organic Solvents*, 5(1) BIOCHEMICAL SOCIETY TRANSACTIONS pp. 274–276 (1977); Crumbliss et al., *Preparation and Activity of Carbonic Anhydrase Immobilized on Porous Silica Beads and Graphite Rods*, 31 BIOTECHNOLOGY AND BIOENGINEERING pp. 796–801 (1988); Cantenys et al., *Covalent Attachment of Insulin to the Outer Surface of Liposomes*, 117 (2) BIOCHEMICAL AND BIOPHYSICAL RESEARCH COMMUNICATIONS, pp. 399–405 (Dec. 16, 1983); Martin et al., *Irreversible Coupling of Immunoglobulin Fragments to Preformed Vesicles*, 257(1) THE JOURNAL OF BIOLOGICAL CHEMISTRY pp. 286–288 (Jan. 10, 1982); and O'Daly et al., *Activity of Carbonic Anhydrase Immobilized on Porous Silica Beads in Organic Media*, 12 BIOTECHNOLOGY AND APPLIED BIOCHEMISTRY, pp. 11–19 (1990). A disadvantage of covalently immobilizing enzymes or proteins on liposomes is that the activity of the enzymes may be altered or substantially decreased. Therefore, it is desirable to provide a means for transporting enzymes and proteins that are immobilized by non-covalent binding.

In U.S. Pat. No. 4,867,917 (Schnur and Singh), incorporated herein in its entirety and for all purposes, a method for synthesizing diynoic acid having the formula:

$$CH_3(CH_2)_n-C\equiv C-C\equiv C-(CH_2)_m COOH \qquad (1)$$

was disclosed wherein n and m are integers from 5–11 and 7–16, respectively. The basic heterocoupling reaction achieved for the formation the above-identified diynoic acids is between:

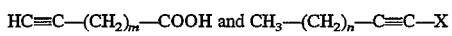

$$HC\equiv C-(CH_2)_m-COOH \text{ and } CH_3-(CH_2)_n-C\equiv C-X$$

wherein X is a selected halogen, preferably iodo, bromo or chloro and where m is 5,6,7,8,9,10, or 11 and where n is 7,8,9,10,11,12,13,14,15, or 16. See column 2, lines 45–70 and the remainder of the Schnur and Singh U.S. Pat. No. 4,867,917 for the synthetic scheme, incorporated herein by reference. It should be noted that the same synthetic scheme outlined in U.S. Pat. No. 4,867,917 for forming the diynoic acids wherein n is between 7–16 and m is between 5–11 can also be successfully used for forming diynoic acids wherein n is between 1–27 (i.e. 1, 2, 3, 4, 5, 6, 7, 8, 9, 10, 11, 12, 13, 14, 15, 16, 17, 18, 19, 20, 21, 22, 23, 24, 25, 26, or 27) and wherein m is between 2–17 (i.e. 2, 3, 4, 5, 6, 7, 8, 9, 10, 11, 12, 13, 14, 15, 16, or 17).

These diynoic acids were useful in forming certain alkadiynoyl-sn-glycero-3-phospholipids. The phospholipids derived from the diynoic acids allow polymerization thereof to form certain microstructures which are peculiarly stable in harsh physical and chemical environments. In particular, the microstructures may be lipid bilayers, tubules, liposomes of various diameters and other microstructures. U.S. Pat. No. 4,867,917 (Schnur and Singh) is incorporated herein by reference in its entirety and for all purposes. The microstructure of phospholipids having the formula:

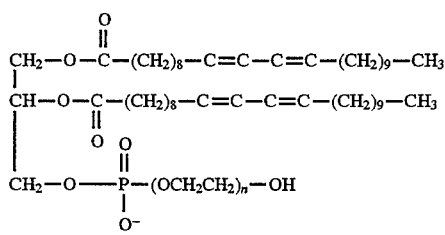

(1a)

where n equals 2 or 3 or 4 are discussed by Markowitz, Schnur and Singh. See Markowitz, M., Schnur, J., and Singh, A., *The influence of the polar headgroups of acidic diacetylenic phospholipids on tubule formation, microstructure morphology and Langmuir film behavior*, 62 CHEMISTRY AND PHYSICS OF LIPIDS, pp. 193–204 (1992), incorporated herein by reference in its entirety and for all purposes. See also Markowitz, M., Baral, S., Brandow, S., and Singh, A., *Palladium ion assisted formation and metallization of lipid tubules*, 224 THIN SOLID FILMS pp. 242–247 (1993), incorporated herein by reference in its entirety and for all purposes. See also Singh, A., and Schnur, J. M., CHAPTER 7-POLYMERIZABLE PHOSPHOLIPIDS in PHOSPHOLIPIDS HANDBOOK, Gregor Cevc (Editor), Marcell Dekker, Inc., New York, pp. 233–291 (1993), incorporated herein by reference in its entirety and for all purposes. It is known that covalent enzyme immobilization on surfaces usually results in substantial loss of enzyme activity. See Wulf G., POLYMERIC REAGENTS AND CATALYSIS, Ford, W. (Editor), ACS Symposium Series 308, American Chemical Society, pp. 186–230, Washington, D.C. (1986). See also Sinha, P. et al., 28A IND. J. CHEM. PP. 33515 (1989). Thus, there is a need for a means to immobilize proteins and/or enzymes by non-covalent binding upon a microstructure such as a liposome or a lipid bilayer wherein the problem of a substantial loss of, for example, enzyme activity associated with covalent binding, is avoided. To date, phosphatidylcholine derivatives for forming polymerized liposomes or bilayers comprising polymerizable metal chelating lipids interspersed within the liposomes or lipid bilayers formed have not been made. There is a need for forming polymerizable metal chelating lipids that can be incorporated into a microstructure, for example, a liposome or a lipid bilayer. There is a need for forming microstructures, for example, liposomes or bilayers wherein polymerizable metal chelating lipids are incorporated into the liposome or the bilayer wherein the polymerizable metal chelating lipid can chelate with metal ions which metal ions can further chelate with proteins or enzymes resulting in non-covalent immobilization of, for example, a protein or an enzyme onto the microstructure. There is a need for forming lipids capable of forming microstructures such as liposomes or bilayers, capable of non-covalently immobilizing proteins and/or enzymes and capable of being polymerized so that the microstructures formed (e.g. liposome or bilayers) do not break apart upon, for example, mild sonication or under working conditions, for example, of pH between about 2 to 11 and temperature of between about 0° C. to about 80° C. See R. L Juliano, S. L Regen, M. Singh, M. J. Hsu and A. Singh, *Stability properties of photopolymerized liposomes*, 1 BIOTECHNOLOGY pp. 882–885 (1983). There is a need for forming polymerized liposomes of variable diameter that are formed from polymerizable non-metal chelating lipids interspersed with polymerizable metal chelating lipids having moieties capable of chelating with metal ions, which metal ions are further capable of chelating with proteins and/or enzymes in order to non-covalently immobilize the proteins and/or enzymes.

SUMMARY OF THE INVENTION

It is therefore an object of the present invention to form polymerizable metal chelating lipids that can be polymerized and interspersed into polymerizable non-chelating lipids to form lipid microstructures.

It is therefore another object of the present invention to form lipid microstructures such as liposomes or bilayers from the polymerization of polymerizable metal chelating lipids and polymerizable non-chelating lipids.

It is therefore yet another object of the present invention to form lipids capable of forming microstructures such as liposomes or bilayers, capable of non-covalently immobilizing proteins and enzymes and also capable of being polymerized so that the microstructures formed (e.g. liposomes or bilayers) do not break apart upon, for example, mild sonication or under working conditions, for example, of pH between about 2 to about 11 and temperature of between about 0° C. to about 80° C.

It is a further object of the present invention to form liposomes that are formed from polymerizable lipids and which lipids are interspersed with polymerizable metal chelating lipids capable of chelating with metal ions, which metal ions are further capable of chelating with proteins and/or enzymes in order to non-covalently immobilize the proteins and/or enzymes.

It is yet a further object of the present invention to form liposomes of variable diameter that are formed from polymerizable non-metal chelating lipids and polymerizable metal chelating lipids capable of chelating with metal ions, which metal ions are further capable of chelating with proteins and/or enzymes in order to non-covalently immobilize the proteins and/or enzymes.

It is an even further object of the present invention to immobilize proteins and/or enzymes by non-covalent binding upon a microstructure such as a liposome or a lipid bilayer wherein the problem of a substantial loss of, for example, enzyme activity associated with covalent binding, is avoided.

These and other objects of the invention are accomplished by the structures and processes hereinafter described as phosphatidyl choline derivatives. Phosphatidyl choline has the formula:

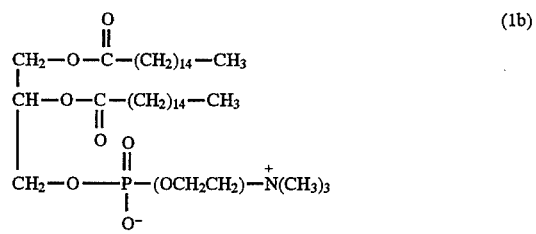

(1b)

The lipids of this invention are derivatives of phosphatidyl choline having the general chemical formula:

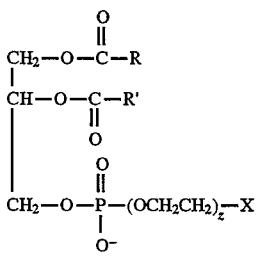

(2)

wherein at least one of R and R' is a polymerizable unsaturated alkyl group, acid or ester, wherein X includes an iminodiacetic acid in the polymerizable metal, chelating lipid (2) and wherein z is an integer from 1–20 including 1 and 20. Lipid microstructures are formed by mixing the polymerizable metal chelating lipid monomers (2) with polymerizable non-chelating lipid monomers wherein X includes a non-chelating group, for example, —$N^+(CH_3)_3$.

BRIEF DESCRIPTION OF THE DRAWINGS

A more complete appreciation of the present invention and several of the accompanying advantages thereof will be readily obtained by reference to the following detailed description when considered in conjunction with the accompanying drawings, wherein.

DETAILED DESCRIPTION OF THE PREFERRED EMBODIMENTS

Figure 1:
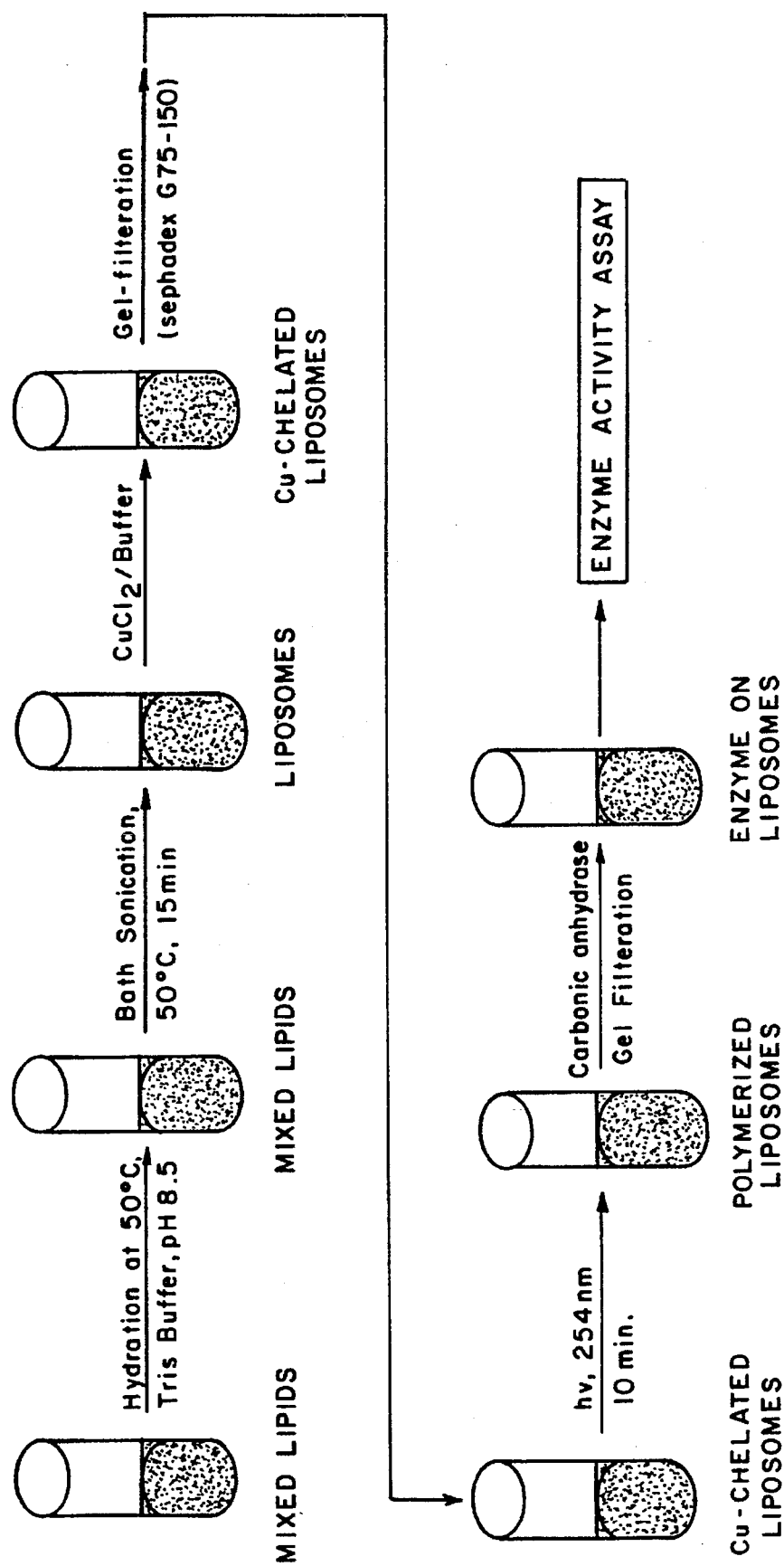
FIG. 1 is a schematic for the steps involved in non-covalent enzyme immobilization wherein the enzyme is bovine carbonic anhydrase.

The following detailed description of the preferred embodiment is provided to aid those skilled in the an in practicing the present invention. However, the following detailed description of the preferred embodiment should not be construed to unduly limit the present invention. Variations and modifications in the embodiments discussed may be made by those of ordinary skill in the art without departing from the scope of the present inventive discovery.

The lipids of this invention have the general chemical formula:

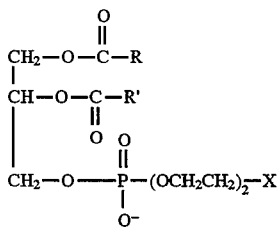

(3)

wherein R and R' are represented by either of the following represented by the formulas:

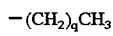

(4)

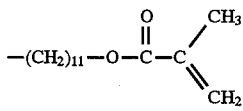

(5)

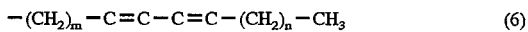

(6)

wherein R and R' may be the same or different, wherein at least one of R and R' is unsaturated, wherein X may be either of the following represented by the formulas:

(7)

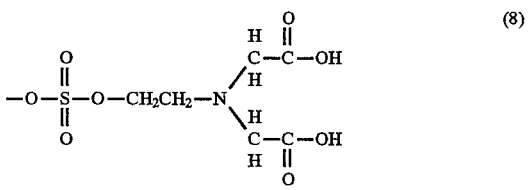

(8)

wherein n, m, q and z are integers, wherein typically $3 \leq (n+m) \leq 29$, more typically $10 \leq (n+m) \leq 29$, preferably $15 \leq (n+m) \leq 29$, more preferably $20 \leq (n+m) \leq 29$ and most preferably $21 \leq (n+m) \leq 27$, wherein q is an integer between 1–20 including 1 or 20, wherein z is an integer between 1–20 including 1 and 20, and wherein X is either of (7) or (8) in the polymerizable metal-chelating lipid monomer. The minimum value for n is 1 and the maximum value for n is 27 and the minimum value for m is 2 and the maximum value for m is 2.8. The values of m and n as depicted in structure (4) can be selected from 1–27 for n and from 2–28 for m by synthesizing the diynoic acid having the desired values for n and m according to the synthetic scheme outlined in U.S. Pat. No. 4,867,917 of Schnur and Singh, incorporated herein in its entirety and for all purposes.

When at least one of R and R' has the structure as depicted in (4), typically, q is between 1 to 20 (i.e. 1, 2, 3, 4, 5, 6, 7, 8, 9, 10, 11, 12, 13, 14, 15, 16, 17, 18, 19, or 20). More typically, q is between 5–18 (i.e. 5, 6, 7, 8, 9, 10, 11, 12, 13, 14, 15, 16, 17, or 18). Preferably, q is between 10–17 (i.e. 10, 11, 12, 13, 14, 15, 16, or 17). More preferably, q is between 11–16 (i.e. 11, 12, 13, 14, 15, or 16). Most preferably, q is between 12–16 (i.e. 12, 13, 14, 15, or 16). Typically, z is between 1 to 20 (i.e. 1, 2, 3, 4, 5, 6, 7, 8, 9, 10, 11, 12, 13, 14, 15, 16, 17, 18, 19, or 20). More typically, z is between 1–15 (i.e. 1, 2, 3, 4, 5, 6, 7, 8, 9, 10, 11, 12, 13, 14, or 15). Preferably, z is between 1–10 (i.e. 1, 2, 3, 4, 5, 6, 7, 8, 9, or 10). More preferably, z is between 1–5 (i.e. 1, 2, 3, 4, or 5). Most preferably, z is between 1–3 (i.e. 1, 2, or 3).

Compound (3), with at least one of R and R' having the structures depicted as (4), (5), or (6), is synthesized by the exemplary base catalyzed acylation of sn-glycero-3-phospho-(N-ethyl)-iminodiacetic acid, (8d), for z=1, the acylation of sn-glycero-3-phospho-(N-ethylenoxy ethyl)-iminodiacetic acid, (8d'), for z=2, and the acylation of sn-glycero-3-phospho-(N-diethylenoxy ethyl)-iminodiacetic acid, (8d"), for z=3, with the appropriate anhydride(s), respectively, according to the methodology in Singh, A., An efficient synthesis of phosphatidylcholines, 31 JOURNAL OF LIPID RESEARCH, pp. 1522–1525 (1990), incorporated herein in its entirety and for all purposes.

The value of z in compound (3) is varied by using the appropriate halophosphodichloridate as illustrated in the exemplary synthesis of (8b), (8b') and (8b") wherein the values of z are 1, 2 and 3, respectively, in the final lipid product, compound (3).

Note that both of the amine moieties of (7) and/or (8) contain an iminodiacetic group (IDA):

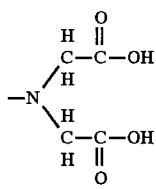
(8a)

The synthesis of the polymerizable metal chelating lipids of structure (3) is shown by the reaction scheme shown on the following page:

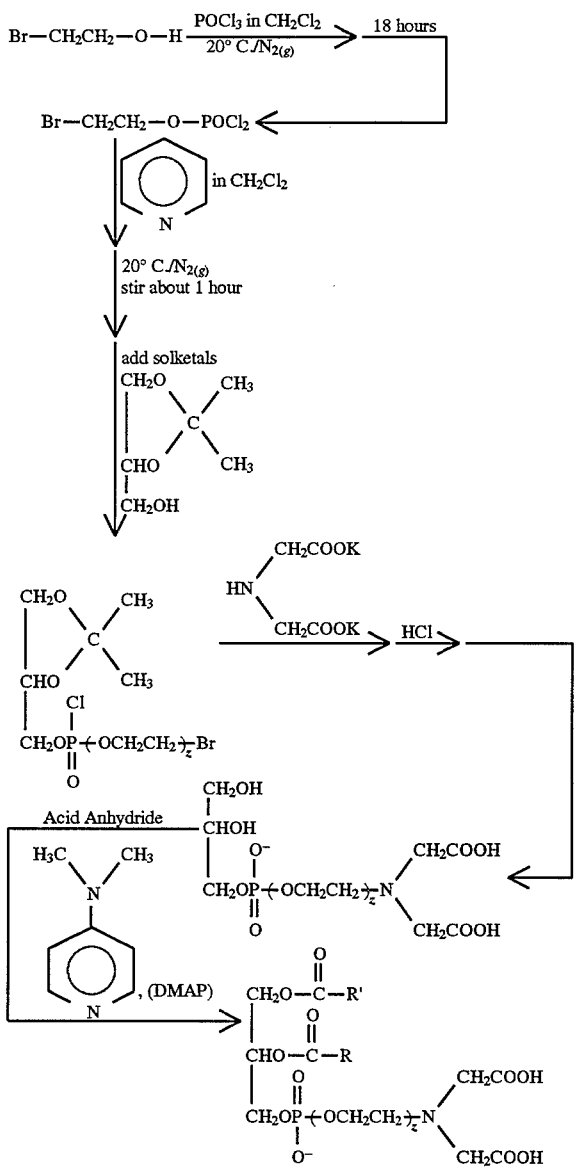

The following examples are given to illustrate specific applications of the invention, including the best mode now known to perform the invention. These specific examples are not intended to limit the scope of the invention described in this application.

2-Bromoethyl phosphodichloridate, (8b):

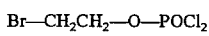
(8b)

Compound (8b) was synthesized following the literature procedure with some modifications. To 85 g of phosphoryl chloride (0.55 mol) dissolved in 100 mL of dry methylene chloride, a solution of 2-bromoethanol (54 g, 0.43 mol) in 30 mL of dry methylene chloride was added dropwise over a period of 30 minutes. The reaction mixture was maintained at 20° C. Dry nitrogen gas was slowly bubbled to remove the HCl gas generated during reaction. After 18 hours, the methylene chloride and excess phosphoryl chloride were removed by rotary evaporation and the crude product was distilled under vacuum to afford 87 g (0.36 mol, 83% yield) of (8b) as colorless liquid. B.P. 76°–77° C./0.05 mm Hg. NMR (CDCl$_3$) $\delta_{ppm}$ 3.56 (t d, OCH$_2$, J=6 Hz, J=1, 2H), 4.56 (t,—CH$_2$Br, J=6 Hz, 1H), 4.60 (t,—CH$_2$Br, J=6.3 Hz, 1H). IR 1300 (P=O), 1070 (P—O—C), 1020 (P—O—C) cm$^{-1}$. Elemental analysis: analyzed for C 9.98%, H 1.58%; found C=9.93%, and H=1.67%.

SYNTHESIS OF 2-Chloroethylenoxy ethyl phosphodicholridate, (8b'):

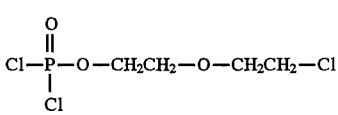
(8b')

2-Chloroethoxyethanol (34 g, 0.27 mol) was added to phosphorous oxytrichloride (52 g, 0.34 mol) under nitrogen. The solution was stirred overnight with nitrogen bubbling to remove the HCl formed. Excess POCl$_3$ was removed under high vacuum and the residue was vacuum distilled to yield (8b') as a colorless liquid 53 g (80%). $^1$H NMR (CDCl$_3$) d 3.59 (td, J=6.1 Hz, 2H), 3.74 (td, J=6.1 Hz, 2H), 3.79(m, 2H), 4.38(m, 2H) IR (neat) 2964, 2872, 1296 (P=O), 1136, 1043 cm$^{-1}$.

SYNTHESIS OF 2-Chlorodiethylenoxy ethyl phosphodichloridate, (8b"):

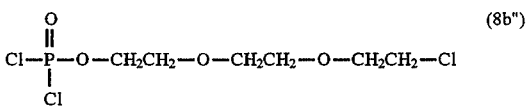
(8b")

2-(2-(2-Chloroethoxyethoxy)ethanol (50 g, 0.30 mol) was added to phosphorous oxytrichloride (35 ml, 57.6 g, 0.37 mmol) under nitrogen. The solution was stirred overnight with nitrogen bubbling to remove the HCl formed. Excess POCl$_3$ was removed under high vacuum and the residual colorless liquid (8b") was left on the vacuum overnight. Yield=81 g (94%). $^1$H NMR (CDCl$_3$) d 3.57 (td, J=6.1 Hz, 2H), 3.63 (overlapping multiplets, 4H), 3.70(dt, J=6.1 Hz, 2H), 3.77( m, 2H), 4.38 (m, 2H) IR (neat) 2958, 2873, 1452, 1354, 1297 (P=O), 1141, 1013, 827 cm$^{-1}$.

SYNTHESIS OF 1,2-isopropylidene-sn-glycero-3-(2-Bromoethyl) phosphate, z=1, (8c):

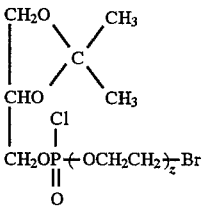
(8c)

To a solution of 2-bromoethyl phosphodichloridate (27.4 g, 0.11 mol) in 50 mL methylene chloride, 9.0 g pyridine (0.11 mole) in dry methylene chloride (20 mL) was added dropwise under nitrogen atmosphere. The reaction temperature was kept at 20° C. throughout the reaction. The resulting solution was stirred for an additional hour before the addition of solketal (14.3 g, 0.11 mole dissolved in 20 mL of methylene chloride). The reaction was stirred for 18 hours at room temperature in dry and inert atmosphere. The resulting phosphochloridate diester was hydrolyzed to phosphate diester by addition of 9.8 g of sodium bicarbonate and water (5 mL) in small portions. After stirring for additional five hours, the reaction mixture was further diluted with methylene chloride, washed with water, dried over sodium sulfate, and solvent was removed under reduced pressure to give 24.6 g of (8c) as colorless liquid in 71% yield. NMR (CDCl$_3$) $\delta_{ppm}$ 1.36 (s, —CH$_3$, 3H), 1.43 (s, —CH$_3$, 3H), 4.00–4.08 (m, —CH$_2$O, 2H), 3.74–3.80 (m,—OCH$_2$—CH$_2$, 2H), 3.49–3.56 (m,—OCH$_2$—CH$_2$Br, 2H), 4.27–4.35 (m, CH—CH$_2$—OP—O, 2H), 4.15 (m, center, CH—, 1H). IR (KBr) 3450 (OH), 1275 (P=O), 1220 (P=O(OH)), 1060 (P—O—C), 1020 (P—O—C) cm$^{-1}$.

SYNTHESIS OF 1,2-isopropylidene glycero-3-chloroethylenoxyethylphosphate, z=2, (8c'):

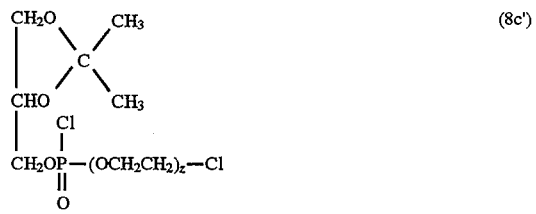

Solketal (8.76 g, 66.2 mmol) was added to an ice cooled solution of dichlorophosphidate (8b') (16.8 g, 69.8 mmol) and triethylamine (9.7 ml, 69.8 mmol) in 25 ml chloroform. The solution was stirred for 17 hours under argon. The reaction was then quenched by the addition of sodium bicarbonate (6.3 g, 75 mmol) and 5 ml water. The chlorofom layer was then washed with water (1×), dried and the solvent evaporated to yield 18 g (90%) of (8c') as a viscous liquid. 1H NMR (CDCl3) d 1.26 and 1.33 (s, 6H), 3.55 (td, J=6,1 Hz, 2H), 3.68(overlapping td and m, J=6, 1 Hz, 6H), 3.98 (m, 2H), 4.09(m, 2H), 4.27 (quintet, 1H) IR (neat) 3486, 2991 2885, 1634, 1454, 1367, 1254, 1214, 1134, 1035 cm$^{-1}$.

SYNTHESIS OF 1,2-isopropylidene glycero-3-chlorodiethylenoxy ethylphosphate, z=3, (8c"):

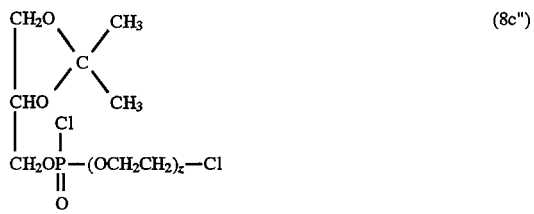

Solketal (8.64 ml, 9.0 g, 68 mmol) was added to an ice cooled solution of dichlorophosphidate (8b") (20 g, 69.5 mmol) and pyridine (5.7 ml, 5.5 g, 70 mmol) in 20 ml chloroform. The solution was stirred for 17 hours under argon. The reaction was then quenched by the addition of sodium bicarbonate (7.0 g, 83 mmol) and 5 ml water. The chlorofom layer was then washed with water (1×), dried and the solvent evaporated to yield 17 g (68%) of (8c") liquid. $^1$H NMR (CDCl$_3$) d 1.17 and 1.24 (s, 6H), 3.48 (overlapping multiplets, 9H), 3.66 (m, 2H), 3.89(m, 3H), 4.03 (m, 2H), 4.15 (quintet, 1H) IR (neat) 3509, 2987, 2888, 1450, 1372, 1298 (P=O), 1217, 1129, 1042, 838, 754 cm$^{-1}$.

SYNTHESIS OF sn-Glycero-3-phospho-(N-ethyl)-iminodiacetic acid, z=1, (8d):

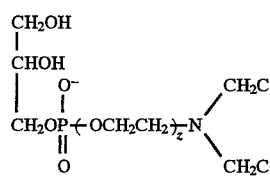

Iminodiacetic acid (5.41 g, 41.3 mmol) was dissolved in 18 mL of 7.0N potassium hydroxide and reacted with 1,2-isopropylidene-sn-glycero-3-(2-bromoethyl)-phosphate, (8c), (18.1 g, 56.7 mmol). The reaction mixture was stirred for four days at room temperature. Unreacted 1,2-isopropylidene-sn-glycero-3-(2-bromoethyl)-phosphate, (8c), (3.9 g) was removed by washing the aqueous layer with methylene chloride. The aqueous layer was concentrated to give 22 g of yellow waxy crude. Potassium bromide resulted from the reaction was removed from the crude product by cooling its methanol solution (200 mL) to 4° C. Potassium bromide crystallized from the solution was filtered off. The volume was reduced and step was repeated until all the KBr is removed. Removal of solvent and drying under high vacuum produced 16.3 g of the intermediate, 1,2-isopropylidene-sn-glycero-3-phospho-(N-ethyl)-iminodiacetic acid potassium salt, as light yellow wax in 88% yield. NMR (D$_2$O) $\delta_{ppm}$ 138 (s, —CH$_3$, 3H), 1.45 (s, —CH$_3$, 3H) 3.58–3.71 (m, —CH$_2$—N, 6H), 3.82–3.96 (m,—POCH$_2$—CH$_2$—, and —OCH$_2$, 4H), 4.03–4.05 (m, —CH—CH$_2$—OP—CH$_2$, 2H), 4.13–4.18 (m, —CHO—, 1H). IR 1640 (COO$^-$), 1245 (P=O), 1080 (P—O—C), 1055 (P—O—C) cm$^{-1}$.

Deprotection of 1,2 diol was carried out by stirring a water solution of the intermediate, 1,2-isopropylidene-sn-glycero-3-phospho-(N-ethyl)-iminodiacetic acid potassium salt, (9.6 g, 21.5 mmol) with 48 mL, 3N HCl for 6 hours. Water was removed and the residue was dissolved in 100 mL of methanol to remove the potassium chloride produced during the reaction. Removal of solvent yielded 6.6 g of residue, which was purified by column chromatography using methanol as eluant. Compound sn-glycero-3-phospho-(N-ethyl) iminodiacetic acid, (8d), was collected as wax in 82% yield (5.8 g). R$_f$=0.75 (2:1 of methanol and 10% of aqueous ammonium acetate) and 0.48 (methanol). NMR (CD$_3$OD) $\delta_{ppm}$ 3.61–3.63 (sharp d, —CH$_2$—N, 4H), 3.68–3.72 (m, —POCH$_2$—CH$_2$—, 2H) 3.75 (q center, —POCH$_2$—CH$_2$—N—, 2H), 3.77–3.86 m center, —CH$_2$O—, 2H), 3.9–3.93 (m, —CH—CH$_2$—OP—, 2H), 4.09–4.2 (m,—CHO—, 1H). IR 1750 (COOH), 1245 (P=O), 1045 (P—O—C) cm$^{-1}$.

SYNTHESIS OF sn-Glycerol-3-phospho (N-2-ethylenoxy ethyl) iminodiacetic acid, z=2, (8d'):

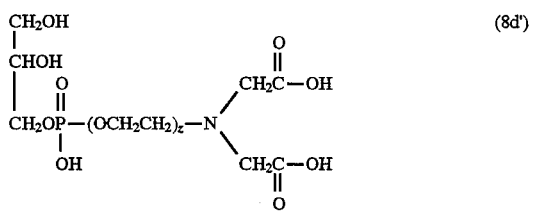

For the exemplary synthesis of (8d'), the corresponding potassium salt was first synthesized from (8c'). Synthesis of the potassium salt, 1,2-Isopropylidene glycero-3-phospho-(N-2-ethylenoxy ethyl) iminodiacetic acid potassium salt, z=2, is given below: Glycerophosphidate (8c') (7.1 g, 22.3 mmol), iminodiacetic acid (2.81 g, 21.1 mmol) and KOH (ca.7M, 10 ml) was stirred for 3 days. The solution was then extracted with dichloromethane to remove unreacted starting material. The water was then evaporated and the residue dissolved in methanol. The precipitate was then removed by repeated concentration and filtration of the methanol solution. Evaporation of methanol gave 7.0 (82%) of 1,2-Isopropylidene glycero-3-phospho-(N-2-ethylenoxy ethyl) iminodiacetic acid potassium salt, z=2 as a waxy solid. $^1$H NMR (D$_2$O) d 1.38 and 1.45 (s, 6H), 2.80(s, 2H), 3.30(s, 4H), 3.59–4.13 (m, 8H), 4.13 (t, 2H), 4.42 (quintet, 1H) IR (neat) 3400, 2995, 2898, 2818, 1600, 1464, 1404, 1331, 1224, 1064, 954, 827 cm$^{-1}$. The 1,2-Isopropylidene glycero-3-phospho-(N-2-ethylenoxy ethyl) iminodiacetic acid potassium salt (1.97 g, 4.0 mmol) was stirred with hydrochloric acid (12 ml, 3M, ca.36 mmol). The HCl was removed under vacuum and the residue dried overnight under vacuum to yield (8d') quantitatively. The residue was dissolved in a known amount of methanol and stored in a freezer (ca. −15° C.). $^1$H NMR (D$_2$O) d 3.46–3.86 (m, 12H), 4.12(s, 4H), 4.21(quintet, 1H) IR (neat) 3506, 2965, 1751, 1654, 1454, 1234, 1127, 1017 cm$^{-1}$.

SYNTHESIS OF sn-Glycerol-3-phospho (N-2-diethylenoxy ethyl) iminodiacetic acid, z=3, (8d"):

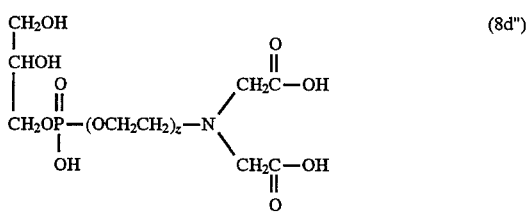

For the exemplary synthesis of (8d"), the corresponding potassium salt was first synthesized from (8c"). Synthesis of the potassium salt, 1,2-Isopropylidene-glycero-3-phospho-(N-2-diethylenoxy ethyl) iminodiacetic potassium salt, is given below:

Glycerophosphidate (8c") (8.44 g, 23.2 mmol), iminodiacetic acid (3.08 g, 23.2 mmol) and KOH (ca.7M, 10 ml) was stirred for 3 days. The solution was then extracted with dichloromethane to remove unreacted starting material. The water was then evaporated and the residue dissolved in methanol. The precipitate was then removed by repeated concentration and filtration of the methanol solution. Evaporation of methanol gave 2.38 g (17%) of 1,2-isopropylidene-glycero-3-phospho-(N-2-diethylenoxy ethyl) iminodiacetic potassium salt as a waxy solid. $^1$H NMR (D$_2$O) d 1.38 and 1.45 (s, 6H), 2.87 (s, 2H), 3.27(s, 4H), 3.62–4.18 (m, 12H) 4.14 (t, 2H), 4.42 (m, 1H) IR (neat) 3331, 2939, 2822, 1628, 1401, 1331, 1244, 1115, 950, 835 cm$^{-1}$.

The 1,2-Isopropylidene-glycero-3-phospho-(N-2-diethylenoxy ethyl) iminodiacetic potassium salt (2.3 g, 4.0 mmol) was stirred with hydrochloric acid (3M, ca.36 mmol). The HCl was removed under vacuum and the residue dried overnight under vacuum to yield (8d") quantitatively. The residue was dissolved in a known amount of methanol and stored in a freezer (ca. −15° C.). $^1$H NMR (D$_2$O) d 3.56–3.96 (m, 16H), 4.23(s, 4H), 4.32 (quintet, 1H) IR (neat) 3352, 2962, 1750, 1644, 1435, 1241, 1045 cm$^{-1}$.

SYNTHESIS OF 1,2 dipalmitoyl-sn-glycero-3-phospho-(N-ethyl)-iminodiacetic acid, z=1, (8e):

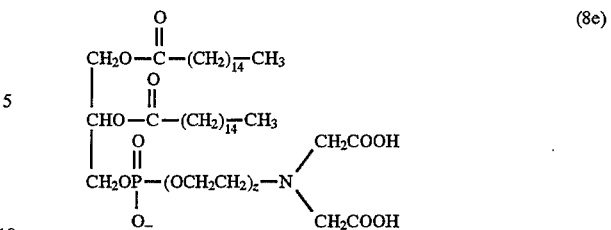

Methanolic solution of sn-glycero-3-phospho-(N-ethyl) iminodiacetic acid, (8d), (180 mg, 0.54 mmol) was transferred to a 25 mL of single-necked, round bottom flask. Methanol was first remove under a stream of nitrogen which left a thin film on the wall of the flask and then by leaving the flask under high vacuum for overnight. To sn-glycero-3-phospho-(N-ethyl) iminodiacetic acid, (8d), was then sequentially added a solution of palmitic anhydride (0.88 g, 1.78 mmol) in 3 mL of chloroform and 4-N,N-dimethylamino pyridine, DMAP, (0.22 g, 1.78 mmol) in 2 mL of chloroform. The resulting suspension was protected from light, and first sonicated at room temperature for 2 hours followed by stirring at room temperature for 24 hours. The course of reaction was followed by thin-layer chromatography (TLC) at various time intervals and considered complete when no changes in the intensity of spot due to the phospholipid were observed. After removing all chloroform, the residue was dissolved in 2 mL of 1 to 1 chloroform-methanol solution and passed through a column of ion exchange resin to remove DMAP. The crude product (816 mg) was then dissolved in chloroform (1 mL) and chromatographed on silica gel column which is treated with 1% acetic acid in chloroform and then washed with chloroform. Elution with chloroform removed about 672 mg of palmitic anhydride and palmitic acid. The phospholipid was eluted with 65:25:4 of chloroform-methanol-water. Fractions were analyzed with TLC. Fractions containing product with same R$_f$ were combined and the solvent was removed to collect 137 mg (31% yield) of 1,2-dipalmitoyl-sn-glycero-3-phospho-(N-ethyl)iminodiacetic acid, z=1, (8e). Using flash column chromatography (chloroform:methanol 95:5 as eluant) increased yields (~40%) of phospholipid in high purity were obtained. R$_f$=0.48 (65:25:4 of chloroform-methanol-water). NMR (CDCl$_3$) $\delta_{ppm}$ 0.87 (t, —CH$_3$, 6H), 1.25 (br s, —(CH$_2$) —, 48H), 1.65 (pentet center, —CH$_2$—CH$_2$—COO, 4H), 2.35 (t center, —CH$_2$—COO, 4H), 3.78 (m center, —CH$_2$—N—(CH$_2$)$_2$—, 6H), 4.8 (m center, —OCH$_2$—, 6H), and 5.3 (m center, —CHO—, 1H). IR (thin film neat) 3200 (br), 2919 (vs), 2851 (vs), 1740 (vs), 1653 (vs) cm$^{-1}$. Elemental analysis: analyzed for C=61.01%, H=9.74%; found C=65.71%, and H=10.88%.

SYNTHESIS OF 1,2-dipalmitoyl-sn-glycero-3-phospho (N-2-ethylenoxy ethyl) iminodiacetic acid, z=2, (8e'):

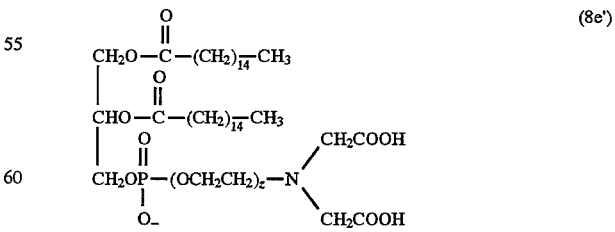

A methanolic solution of 1,2-isopropylidene glycero-3-phospho(N-2-ethylenoxy ethyl) iminodiacetic acid, (8d'), was transferred to a dry flask. The MeOH was evaporated using a stream of dry nitrogen. The residue was then dried under vacuum for 16h prior to use. Palmitic anhydride (0.88 g, 1.77 mmol), DMAP (0.22 g, 1.77 mmol) and 5 ml dry chloroform was added to the 1,2-isopropylidene glycero-3-phospho(N-2-ethylenoxy ethyl) iminodiacetic acid, (8d'), residue (0.22 g, 0.98 mmol). The suspension was sonicated for 2h at room temperature and stirred for 3 days. The solvent was evaporated and the residue dissolved in 1:1 chloroform/methanol and then eluted from AG-50W X8 acidic ion exchange resin. The solvent was evaporated from the eluate and the residue chromatographed using chloroform/methanol (gradient elution) to yield 0.29 g (35%) of the lipid, z=2, (8e'). Rf=0.45 (65:25:4 chloroform:methanol:water) 1H NMR (CDCl3, ppm) d 0.87 (t, 6H), 1.25 (brm, 48H), 1.58 (m, 4H), 2.31 (t, 4H), 3.55–4.6 (m, 16H), 5.24 (m, 1H) IR (film) 3326, 2918, 2854, 1734, 1554, 1461, 1260, 1220, 1100, 1030 cm$^{-1}$.

SYNTHESIS OF 1,2-dipalmitoyl-sn-glycero-3-phospho (N-2-diethylenoxy ethyl) iminodiacetic acid, z=3, (8e"):

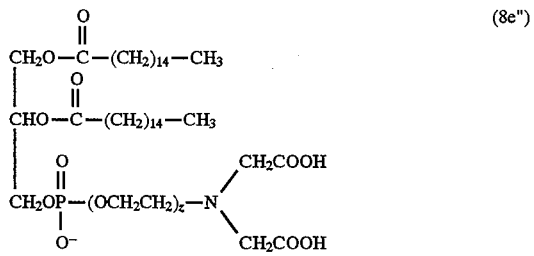

(8e")

A methanolic solution of 1,2-isopropylidene glycero-3-phospho(N-2-diethylenoxy ethyl) iminodiacetic acid, (8d"), was transferred to a dry flask. The MeOH was evaporated using a stream of dry nitrogen. The residue was then dried under vacuum for 16h prior to use. Palmitic anhydride (1.30 g, 2.62 mmol), DMAP (0.40 g, 3.26 mmol) and 5 ml dry chloroform was added to the 1,2-isopropylidene glycero-3-phospho(N-2-diethylenoxy ethyl) iminodiacetic acid, (8d"), residue (0.37 g, 0.98 mmol). The suspension was sonicated for 2h at room temperature and stirred for 3 days. The solvent was evaporated and the residue dissolved in 1:1 chloroform/methanol and then eluted from AG-50W X8 acidic ion exchange resin. The solvent was evaporated from the eluate and the residue chromatographed to yield 140 mg (16%) of the lipid, z=3, (8e"). Rf=0.45 (65:2.5:4 chloroform:methanol:water) 1H NMR (CDCl3, ppm) d 0.86 (t, 6H), 1.25 (brm, 48H), 1.60 (m, 4H), 2.29 (t, 4H), 3.55–4.6 (m, 16H), 5.22 (m, 1H) IR (film) 3326, 2918, 2854, 1734, 1554, 1461, 1260, 1220, 1100, 1030 cm$^{-1}$.

Synthesis of 1,2-Bis(tricosa-10,12-diynoyl)-sn-glycero-3-phospho-(N-ethyl) iminodiacetic acid, z=1, (8f), is shown by the reaction scheme shown below:

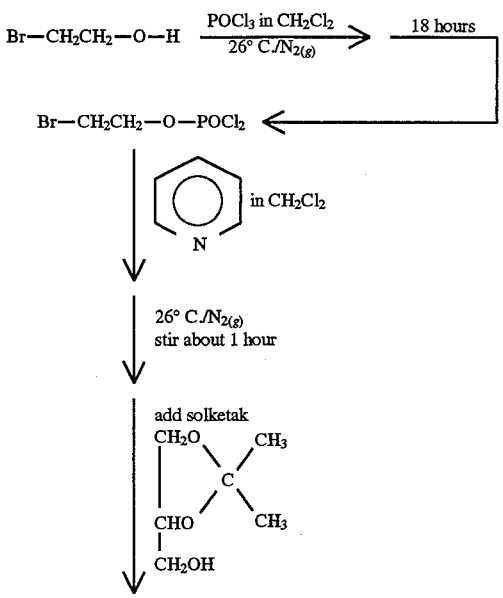

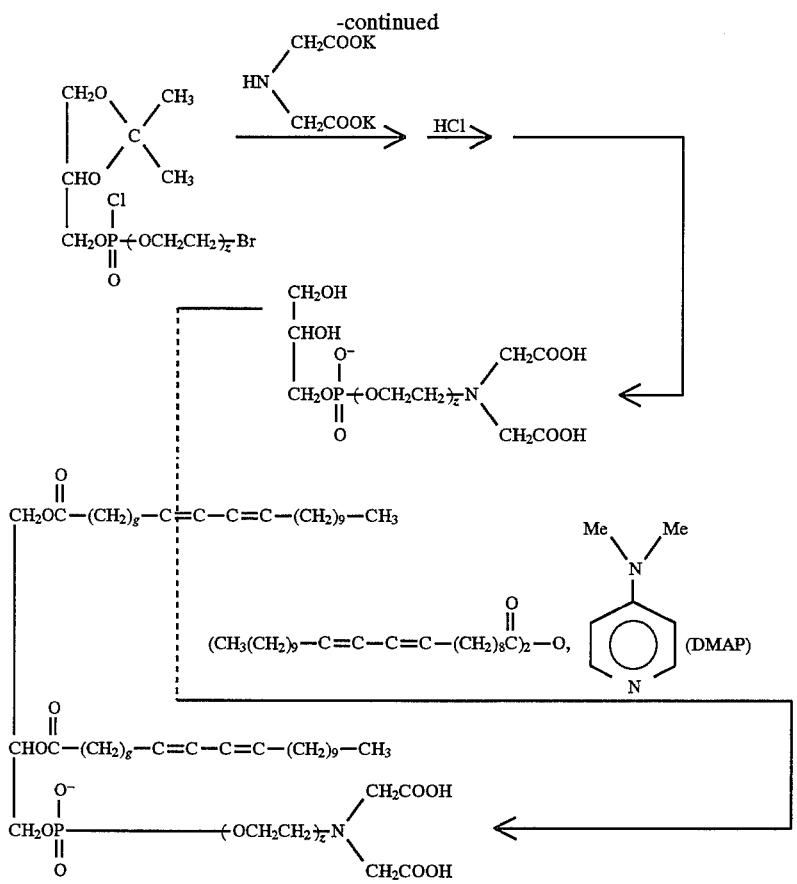

SYNTHESIS OF 1,2-Bis(tricosa-10,12-diynoyl)-sn-glycero-3-phospho-(N-ethyl)-iminodiacetic acid, z=1, (8f):

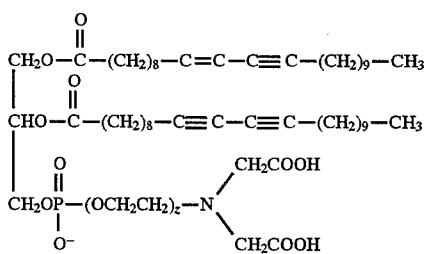

Following the procedure described for 1,2-dipalmitoyl-sn-glycero-3-phospho-(N-ethyl)-iminodiacetic acid, (8e), 0.17 g (0.50 mmol) of sn-glycero-3-phospho-(N-ethyl)-iminodiacetic acid, (8d), was reacted with tricosa-10,12-diynoic anhydride (1.16 g, 1.72 mmol) and DMAP (0.21 g, 1.72 mmol). Special care were taken to protect the reaction mixture from the fluorescent laboratory lights to prevent diacetylene polymerization. DMAP was removed by ion exchange resin and the lipid 1,2-bis(tricosa-10,12-diynoyl)-sn-glycero-3-phospho-(N-ethyl)-iminodiacetic acid, (8f), was separated from the crude by flash chromatography. Chloroform: methanol (95:5) solvent removed all the acid and the lipid was eluted by using 10% methanol in chloroform. In this way 150 mg (31% yield) of pure 1,2-bis(tricosa-10,12-diynoyl)-sn-glycero-3-phospho-(N-ethyl)-iminodiacetic acid, (8f), was collected. $R_f$=0.53 (65:25:4 of chloroform-methanol-water). NMR (CDCl$_3$) $\delta_{ppm}$ 0.87 (t, —CH$_3$, 6H), 1.2–1.8 (br s, —(CH$_2$)—, 56H), 2.35 (m center, —CH$_2$—COO, and —CH$_2$—C≡C—, 12H), 3.78 (m center, —CH$_2$—N—(CH$_2$)$_2$—, 6H), 4.8 (m center, —OCH$_2$—, 6H), and 5.3 (m center, —CHO—, 1H). IR (neat film) 3200 (br), 2925 (vs), 2845 (vs), 2257 (w), 2164 (w), 1741 (vs), 1628 (vs) cm$^{-1}$. Elemental analysis: analyzed for C 63.28%, H 9.07%; found C=66.84%, and H=9.18%.

SYNTHESIS OF 1,2-bis(tricosa-10,12-diynoyl)-sn-glycero-3-phospho-(N-ethylenoxy ethyl)-iminodiacetic acid, z=2, (8f'):

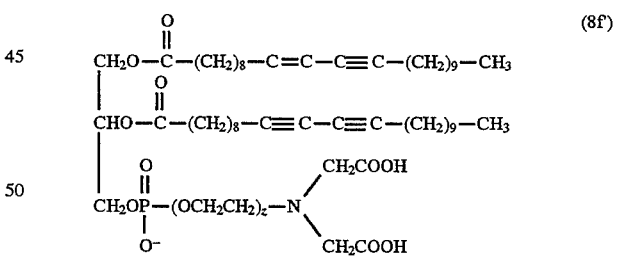

A methanolic solution of 1,2-isopropylidene glycero-3-phospho(N-2-ethylenoxy ethyl) iminodiacetic acid, (8d'), was transferred to a dry flask. The MeOH was evaporated using a stream of dry nitrogen. The residue was then dried under vacuum for 16 hours prior to use. Diacetylenic anhydride (1.39 g, 2.06 mmol), DMAP (0.25 g, 2.06 mmol) and 17 ml dry chloroform was added to the 1,2-isopropylidene glycero-3-phospho(N-2-ethylenoxy ethyl) iminodiacetic acid, (8d'), residue (0.26 g, 0.68 mmol). The suspension was sonicated for 2h at room temperature and stirred for 7 days. The solvent was evaporated and the residue dissolved in 1:1 chloroform/methanol and then eluted from AG-50W X8 acidic ion exchange resin. The solvent was evaporated from the eluate and the residue chromatographed using chloroform/methanol (gradient elution) to yield 0.29 g(41%)

of the lipid, z=2, (8f'). Rf=0.49 (65:25:4). 1H NMR (CDCl3, ppm). d 0.83(t, 6H), 1.22 (brm, 56H), 1.44 (m, 4H), 2.19 (t, 12H), 3.35–4.50 (m, 16H), 5.10 (m, 1H). IR (film) 3394, 3055, 2925, 2855, 2305, 2160, 1735, 1652, 1456, 1265, 1066, 976 cm$^{-1}$.

SYNTHESIS OF 1,2-bis(tricosa-10,12-diynoyl)-sn-glycero-3-phospho-(N-2-diethylenoxy ethyl)-iminodiacetic acid, z=3, (8f''):

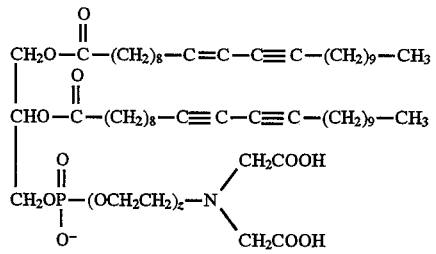

A methanolic solution of 1,2-isopropylidene glycero-3-phospho(N-2-diethylenoxy ethyl)-iminodiacetic acid, (8d''), was transferred to a dry flask. The MeOH was evaporated using a stream of dry nitrogen. The residue was then dried under vacuum for 16h prior to use. Diacetylenic anhydride (1.10 g, 1.60 mmol), DMAP (0.34 g, 2.78 mmol) and 5 ml dry chloroform was added to the 1,2-isopropylidene glycero-3-phospho(N-2-diethylenoxy ethyl)-iminodiacetic acid, (8d''), residue (0.20 g, 0.54 mmol). The suspension was sonicated for 2 hours at room temperature and stirred for 3 days. The solvent was evaporated and the residue dissolved in 1:1 chloroform/methanol and then eluted from AG-50W X8 acidic ion exchange resin. The solvent was evaporated from the eluate and the residue chromatographed over silica gel using chloroform/methanol (gradient elution) to yield 107 mg(18%) of the lipid, z=3, (8f''). Rf=0.48 (65:25:4 chloroform:methanol:water). 1H NMR (CDCl3, ppm) d 0.87(t, 6H), 1.25 (brm, 56H), 1.50 (m, 4H), 2.23 (m, 12H), 3.15–4.75(m, 20H), 5.11 (m, 1H) IR (film) 3547, 2928, 2855, 2251, 2162, 1737, 1618, 1465, 1265, 1168, 1106, 1066, 976 cm$^{-1}$.

SYNTHESIS OF IDA lipid with methacrylate acyl chain, z=1, (8g):

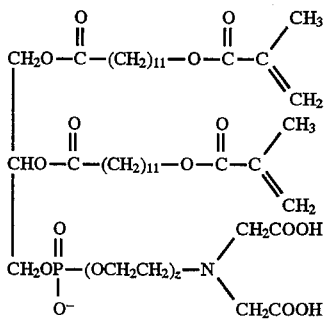

The synthesis of (8g) wherein z=1 is accomplished using the anhydride $(CH_2=C(CH_3)COO(CH_2)_{11}CO—)_2—O$. The anhydride $(CH_2=C(CH_3)COO(CH_2)_{11}CO—)_2—O$ was synthesized according to S. L Regan, A. Singh, G. Oehme, and M. Singh, *Polymerized phosphatidylcholine vesicles: Synthesis and characterization* J. AMER. CHEM. SOC. 104:791–795 (1992), incorporated herein by reference in its entirety and for all purposes. The synthesis of (8g) is accomplished by reacting the anhydride $(CH_2=C(CH_3)COO(CH_2)_{11}CO—)_2—O$ with (8d) according to a similar procedure described in the synthesis of (8e) and (8f).

SYNTHESIS OF IDA lipid with methacrylate acyl chain, z=2, (8g'):

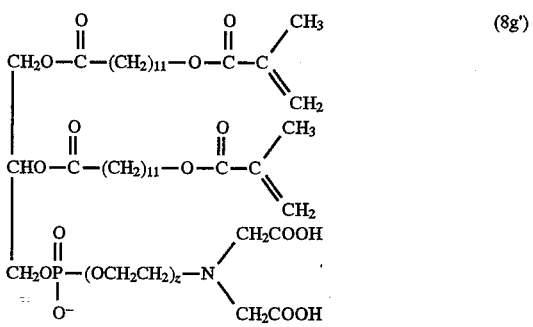

The synthesis of (8g') wherein z=2 is accomplished using the anhydride $(CH_2=C(CH_3)COO(CH_2)_{11}CO—)_2—O$. The anhydride $(CH_2=C(CH_3)COO(CH_2)_{11}CO—)_2—O$ was synthesized according to S. L. Regan, A. Singh, G. Oehme, and M. Singh, *Polymerized phosphatidylcholine vesicles: Synthesis and characterization* J. AMER. CHEM. SOC. 104:791–795 (1992), incorporated herein by reference in its entirety and for all purposes. The synthesis of (8g') is accomplished by reacting the anhydride $(CH_2=C(CH_3)COO(CH_2)_{11}CO—)_2—O$ with (8d') according to a similar procedure described in the synthesis of (8e) and (8f).

SYNTHESIS OF IDA lipid with methacrylate acyl chain, z=3, (8g''):

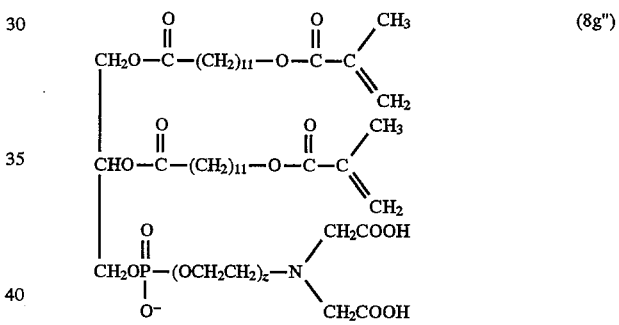

The synthesis of (8g'') wherein z=3 is accomplished using the anhydride $(CH_2=C(CH_3)COO(CH_2)_{11}CO—)_2—O$. The anhydride $(CH_2=C(CH_3)COO(CH_2)_{11}CO—)_2—O$ was synthesized according to S. L Regan, A. Singh, G. Oehme, and M. Singh, *Polymerized phosphatidylcholine vesicles: Synthesis and characterization* J. AMER. CHEM. SOC. 104:791–795 (1992), incorporated herein by reference in its entirety and for all purposes. The synthesis of (8g'') is accomplished by reacting the anhydride $(CH_2=C(CH_3)COO(CH_2)_{11}CO—)_2—O$ with (8d'') according to a similar procedure described in the synthesis of (8e) and (8f).

The scheme for the synthesis of another-of the polymerizable metal chelating lipids is shown on the following page:

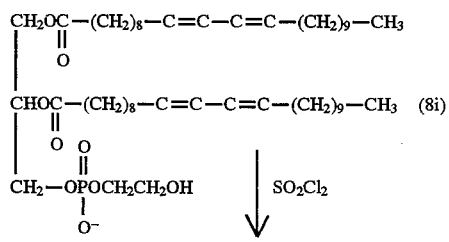

-continued

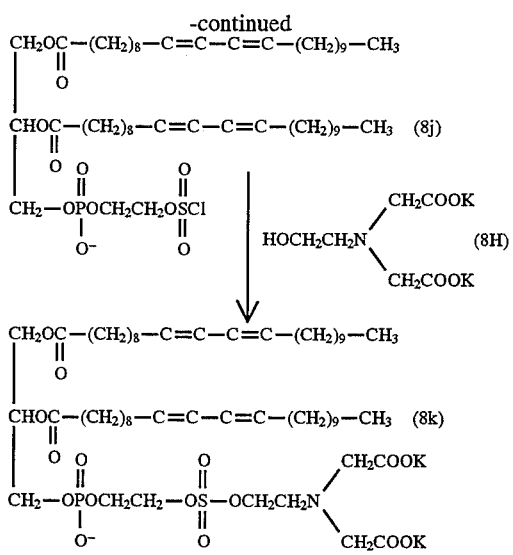

Synthesis of N-(2-hydroxyethyl) iminodiacetic acid (8h):

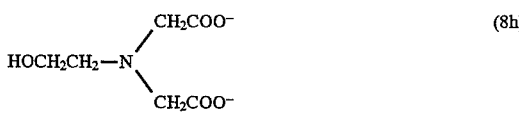

Iminodiacetic acid (IDA) 2.66 g. (20 mmol) dissolved in 9 mL, 7N aqueous KOH was reacted with bromoethanol (6.2 g, 49 mmol) by stirring the mixture at 20° C. for 72 hrs. The reaction was monitored by TLC employing methanol:10% ammonium acetate (2:1) as solvent system. Starting material IDA moved slower ($R_f$=0.28) than that of (8h) ($R_f$=0.4). The solvent was removed and the residue was washed with methanol. Methanol solution contained the title compound and unreacted bromoethanol. Compound (8h) was separated from the reaction mixture first by column chromatography using methanol:ammonium acetate solvent system. The chromatographed product contained ammonium acetate as contaminant which was removed by dissolving the compound in methanol and crystallizing out the salt. Removal of the solvent provided 0.8 g (23% yield) of pure (8h). NMR ($D_2O$) $\delta_{ppm}$ 3.2 (t center,HO—$CH_2$—$CH_2$—N, 2H), 3.66 (s, —$CH_2$—N—($CH_2$)$_2$, 4H), and 3.71 (t center, HO—$CH_2$—$CH_2$—N, 2H). IR 1640 ($COO^-$) $cm^{-1}$.

SYNTHESIS OF 1,2-Bis(tricosa-10,12-diynoyl)-sn-glycero-3-phospho-ethylene-(N-ethyl iminodiacetic acid) sulfate, (8k):

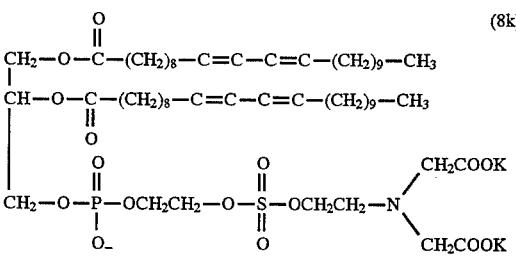

Compound (8i) (169 mg, 0.19 mmol) was reacted 10 fold excess of sulfuryl chloride in chloroform at room temperature. The HCl generated during the reaction mixture was removed by a gentle stream of dry nitrogen bubbled through the solution. The completion of the reaction was confirmed by TLC (2 hours). TLC plates developed with chloroform, methanol, water (65:25:4 v/v) solvent system revealed an $R_f$ of 0.67, which was higher than that of compound (8i) (0.50);

Chloroform and excess sulfuryl chloride were removed under vacuum to give (8j). NMR ($CDCl_3$) $\delta_{ppm}$ 0.88 (t, $CH_3$, 6H), 1.25 (m with an emerging s, —($CH_2$)—, 44H), 1.71 (m center, —$CH_2$—$CH_2$—COO, and —$CH_2$—$CH_2$—C≡C—, 12H), 2.24–2.50 (m center, —$CH_2$—COO, and —$CH_2$—C≡C—, 12H), 4.41–4.51 (m,—$OCH_2$, 8H), and 5.18–5.33 (m center, —CHO—, 1H).

Synthesis of phospholipid (8k) was accomplished by reacting (8j) with (8h). Compound (8j) was used without further purification. The reaction mixture in chloroform was stirred at room temperature under nitrogen atmosphere. TLC analysis at an interval of 2 hours indicated that the reaction reaches to completion within 24 hours. Chromatography of the crude reaction product (8k) on a silica column, developed with chloroform:methanol:water (65:25:4), afforded 69 mg (36%) of a product which was revealed as a single spot on TLC in the same solvent system as used for column chromatography ($R_f$=0.59). NMR ($CDCl_3$) $\delta_{ppm}$ 0.88 (t, $CH_3$, 6H), 1.25 (br s, —($CH_2$)—, 44H), 1.71 (m center, —$CH_2$—$CH_2$—COO, and —$CH_2$—$CH_2$—C≡C—, 12H), 2.24–2.50 (m center, —$CH_2$—COO, and —$CH_2$—C≡C—, 12H), 3.7 (m center, —N—($CH_2$—COOH)$_2$, 4H), 3.9–4.6 (m,—$OCH_2$, 8H), and 5.15–5.41 (m center, —CHO—, 1H). IR (film) 2217 (vw,br), 1460 (S=O), 1244 (PO), 1337 (SO) $cm^{-1}$. Elemental analysis: analyzed for C 65.28%, H 9.46%; found C=70.15%, and H=9.81%.

When making structures (2) and (3) wherein R≠R', synthetic methodology for forming non-similar headgroups (i.e. R≠R') from Singh, A., Schnur, J. M., POLYMERIZABLE PHOSPHOLIPIDS IN PHOSPHOLIPID HANDBOOK, Cevc, C. Ed. Marcel Dekker Inc., N.Y. pp. 233–287 (1993), incorporated herein by reference in its entirety and for all purposes, is to be followed.

The microstructures (e.g. liposomes) of this invention are formed from the above-described polymerizable metal chelating lipids and other phosphatidyl derivatized polymerizable lipids that do not contain functionalities capable of chelating to metal ions.

These polymerizable non-chelating lipids may have the following formula:

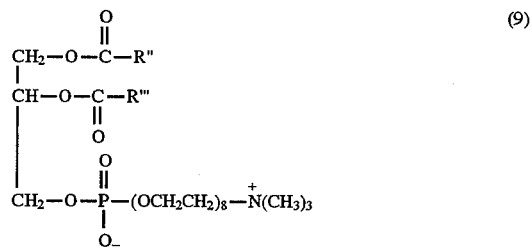

wherein R" and R'" are either of the following:

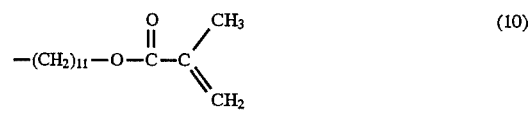

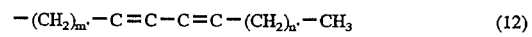

wherein at least one of R" and R'" is polymerizable with itself (i.e. structure (9)) or with structure (3) (i.e. structure (3) with X as either (7) and/or (8)), wherein at least one of R" and R'" is an unsaturated moiety of 1–20 carbon atoms capable of polymerization, wherein R" and R'" may be the same or different, wherein s is an integer between 1–20 including 1 and 20, wherein q' is an integer between 1 and 20 including 1 and 20 and wherein n' and m' are integers. When at least one of R" and R'" has the structure as depicted in (12), typically 3≦(n'+m')≦29, more typically 10≦(n'+m')≦29, preferably 15≦(n'+m')≦29, more preferably 20≦(n'+m')≦29 and most preferably 21≦(n'+m')≦27. The minimum value for n' is 1 and the maximum value for n' is 27 and the minimum value for m' is 2 and the maximum value for m' is 2.8. The values of m' and n' as depicted in structure (12) can be selected from 1–27 for n' and from 2–28 for m' by synthesizing the diynoic acid having the desired values for n' and m' according to the synthetic scheme outlined in U.S. Pat. No. 4,867,917 of Schnur and Singh, incorporated herein in its entirety and for all purposes. When at least one of R" and R'" has the structure as depicted in (11), typically, q' is between 1 to 20 (i.e. 1, 2, 3, 4, 5, 6, 7, 8, 9, 10, 11, 12, 13, 14, 15, 16, 17, 18, 19, or 20). More typically, q' is between 5–18 (i.e. 5, 6, 7, 8, 9, 10, 11, 12, 13, 14, 15, 16, 17, or 18). Preferably, q' is between 10–17 (i.e. 10, 11, 12, 13, 14, 15, 16, or 17). More preferably, q' is between 11–16 (i.e. 11, 12, 13, 14, 15, or 16). Most preferably, q' is between 12–16 (i.e. 12, 13, 14, 15, or 16). Typically, s is between 1 to 20 (i.e. 1, 2, 3, 4, 5, 6, 7, 8, 9, 10, 11, 12, 13, 14, 15, 16, 17, 18, 19, or 20). More typically, s is between 2–20 (i.e. 2, 3, 4, 5, 6, 7, 8, 9, 10, 11, 12, 13, 14, 15, 16, 17, 18, 19, or 20). Preferably, s is between 3–15 (i.e. 3, 4, 5, 6, 7, 8, 9, 10, 11, 12, 13, 14, or 15). More preferably, s is between 4–10 (i.e. 4, 5, 6, 7, 8, 9, or 10). Most preferably, s is between 4–6 (i.e. 4, 5 or 6).

Compound (9) with at least one of R" and R'" having the structures depicted as (10), (11), or (12) is synthesized by the base catalyzed acylation of sn-glycero-3-phosphocholine with the appropriate anhydride(s) according to the methodology in Singh, A., *An efficient synthesis of phosphatidylcholines*, 31 JOURNAL OF LIPID RESEARCH, pp. 1522–1525 (1990), incorporated herein in its entirety and for all purposes.

SYNTHESIS OF 1,2-bis(tricosa-10,12-diynoyl)-sn-glycero-3-phosphocholine, (13):

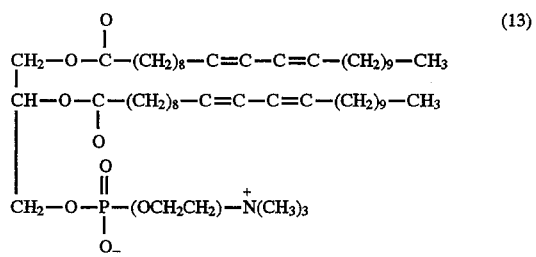

All chemicals used in this work were purchased from Aldrich Chemical Co. Diacetylenic lipid, 1,2-bis(tricosa-10,12-diynoyl)-sn-glycero-3-phosphocholine, was synthesized following the procedure developed in our lab. See Singh, A., *An efficient synthesis of phosphatidylcholines*, 31 JOURNAL OF LIPID RESEARCH, pp. 1522–1525 (1990), incorporated herein in its entirety and for all purposes. Synthetic intermediates and lipids were characterized by IR (Perkin-Elmer 1800 FT-IR), and NMR (Brucker MSL-360 300 MHz) Spectrometer. IR spectra were taken in KBr pellet or as thin film. For column chromatography and TLC analysis, silica gel 60, 70–230 mesh and silica gel 60 $F_{254}$ (both E. Merck) were used. For flash chromatography 230–400 mesh Merck grade 60 silica gel was used. Cationic impurities were removed by using Biorad resin AG 50W-X8, 200–4000 mesh. Ultrasound agitation was carried out on a NEY 300 ultrasonic bath. The lipids on TLC plates were visualized by a combination of three techniques; UV, iodine spray, and molybdenum blue spray.

When making structure (9) wherein R"≠R'", synthetic methodology for forming non-similar headgroups (i.e. R"≠R'") from Singh, A., Schnur, J. M., POLYMERIZABLE PHOSPHOLIPIDS IN PHOSPHOLIPID HANDBOOK, Cevc, C., Ed., Marcel Dekker Inc., N.Y. pp. 233–287 (1993), incorporated herein by reference in its entirety and for all purposes, is to be followed.

The microstructures of the presently claimed invention are formed by mixing lipid monomers having the formula (3) (i.e. structure (3) with X as either (7) and/or (8)), with lipid monomers having the formula (9). Typically, the microstructures (e.g. liposomes) of the present invention contain 1–60 mole % lipid molecules of structure (3) and the remaining 40–99 mole % lipid molecules of structure (9). Preferably, the microstructures (e.g. liposomes) of the present invention contain 5–50 mole % lipid molecules of structure (3) and the remaining 50–95 mole % lipid molecules of structure (9). More preferably, microstructures (e.g. liposomes) of the present invention contain 10–40 mole % lipid molecules of structure (3) and the remaining 60–90 mole % lipid molecules of structure (9). Even more preferably, microstructures (e.g. liposomes) of the present invention contain 10–20 mole % lipid molecules of structure (3) and the remaining 80–90 mole % lipid molecules of structure (9). Most preferably, microstructures (e.g. liposomes) of the present invention contain 10–15 mole % lipid molecules of structure (3) and the remaining 85–90 mole % lipid molecules of structure (9).

The liposomes formed have variable diameters. Typically, the liposomes formed, as described above, have a diameter of between about 500–10,000Å. More typically, the liposomes formed, as described above, have a diameter of between about 600–5,000Å. Preferably, the liposomes formed, as described above, have a diameter of between about 700–2,500Å. More preferably, the liposomes formed, as described above, have a diameter of between about 800–2,000Å. Most preferably, the liposomes formed, as described above, have a diameter of between about 900–1,300Å.

Steps involved in the formation of the liposomes, binding of the copper to the liposomes formed, polymerization of the lipids of the liposomes formed and the further non-covalent binding of an enzyme or a protein having histidine residues, for example, bovine carbonic anhydrase, to the liposomes is outlined in FIG. 2 and further described in the examples below.

Note that the lipids formed according to the present invention are further formed into microstructures such as liposomes. The strategy of the presently claimed invention relies on hydrogen bonds or electrostatic forces in the immobilization of proteins or enzymes onto the formed microstructures such as enzymes. The concept is to immobilize a macromolecule such as a protein or an enzyme by coordinating the binding sites of the macromolecule (e.g. a protein or an enzyme) to a metal ion which metal ion is already complexed with a metal chelating phospholipid. While the following examples have focused on iminodiacetic acid (IDA) moiety as the chelating site on the phospholipid headgroup, $Cu^{+2}$ as the chelating metal ion and histidine containing macromolecules (e.g. proteins or enzymes), the present invention can be extended by linking other types of functional moieties as the chelating site on the phospholipid, other metal ions as the chelating metal ions and other types of macromolecules which have an affinity towards the functional moieties available as the chelating sites on the target lipid molecules selected for forming microstructures such as liposomes according to the presently disclosed invention.

Example Preparation of liposomes:

Polymerizable lipid (13) was mixed with non-polymerizable metal chelating lipid (z=1, 8e) in a ratio of 90:10 (mole:mole), respectively, to form SET (1) in glass tubes using chloroform as solvent. Likewise, polymerizable lipid (13) was mixed with polymerizable metal chelating lipid (z=1, 8f) in a ratio of 90:10 (mole:mole), respectively, to form SET (2) in glass tubes using chloroform as solvent. The solvent was removed to form a thin lipid film on the wall of the glass tubes. The vacuum dried (4 hours) thin lipid films of SET (1) and SET (2), respectively, were dispersed in 2 mL, 0.05M Tris-HCl (Tris buffer, pH=8.5) by incubating at 55° C. for two hours followed by sonication at 50° C. for 12 minutes in a bath sonicator. Sonication was carried out until a dispersion with constant turbidity at 400 nm was achieved.

Binding of Copper to the liposomes:

The liposomes of SET (1) and SET (2) were then treated with 0.01 mM $CuCl_2$ in the 0.05M Tris-HCl (Tris buffer, pH=8.5) to form the Cu bound liposomes, respectively. A small amount of precipitation of the liposomes was observed which dispersed upon vortex mixing. The unbound copper salt was removed by gel filtration on a Sephadex G 75–125 column. The copper bound liposomes of SET (1) and SET (2) were collected in the void volume during gel-filtration (7.5 mL) while the free copper eluted in fractions collected after 20 mL. The fractions with free copper salt were visible due to their intense blue color. Copper bound liposomes were divided into two equal volumes for each of SET (1) and SET (2) to form SET (1a), SET (1b), SET (2a) and SET (2b), respectively.

Example Polymerization of Copper bound liposomes:

SET (1a) and SET (2a) were polymerized at 4° C. by irradiating with 254 nm light for 10 minutes. Polymerization produced an orange to reddish color dispersion. Polymerization was confirmed by TLC analysis. Most of the lipid from SET (1a) and SET (2a) was found at the origin of the TLC plate.

Example Non-covalent binding of Carbonic Anhydrase to Copper bound liposomes of SET (1a), SET (2a), SET (1b) and SET (2b):

This step involves the selection of an enzyme which consist of several exposed histidine residues. Bovine carbonic anhydrase II was found to be an ideal choice, since it contains six histidine residues, four of them available within a distance of 6Å. The enzyme bovine carbonic anhydrase was bound to the surface of copper bound liposomes of SET (1a), SET (2a), SET (1b) and SET (2b). Binding was possible due to the non-covalent binding or chelating of the $Cu^{+2}$ on the surface of the liposomes further chelating (i.e. non-covalent binding) with the histidine residues of carbonic anhydrase. After addition of the bovine carbonic anhydrase, the liposomes from SET (1a), SET (2a), SET (1b) and SET (2b) were subjected to gel filtration and were collected as fractions of the void volume (7.5 mL), respectively. The fractions collected were monitored at 400 nm for the presence of liposomes. The average liposome size for each of the sets was found to be about 1300Å.

Example General Procedure for Enzyme Assay:

Enzyme assays were performed using a Durrum Stopped-Flow Spectrophotometer equipped with an A/D converter and the OLIS stopped-flow operating system from Online Instrument Systems, Inc. (Jefferson, Ga.). One syringe of the stopped-flow spectrophotometer was loaded with substrate (5 mM p-nitrophenyl acetate in 30% acetone/water) and the other syringe was loaded with the preparation to be tested (i.e. fractions collected from SET (1a), SET (2a), and SET (2b) after having exposed the liposomes to both copper and the enzyme bovine carbonic anhydrase) in 100 mM Tris buffer (pH=8.5). Data was collected at the rate of 200 points in 120 seconds. Absorbance was monitored at 402 nm with a slit width set to 1.0. Data was analyzed using the "DATAFIT" module of the stopped-flow operating system. All data analyzed were fit with linear regression.

Enzyme assays were performed on the fractions collected from SET (1a), SET (2a), and SET (2b) after having exposed the liposomes to both copper and the enzyme bovine carbonic anhydrase. The results of the enzyme assays performed are illustrated in FIG. 2. Note that in SET (2a) of FIG. 2 wherein lipids (8f) and (13) were polymerized, the RELATIVE activity of the carbonic anhydrase attached to the polymerized liposomes via the chelated copper ions is greater than the activity of the enzyme alone (at 0.8 µg/ml concentration of enzyme alone) as measured by the reaction rate determined by the enzyme assay described above.

Figure 2:
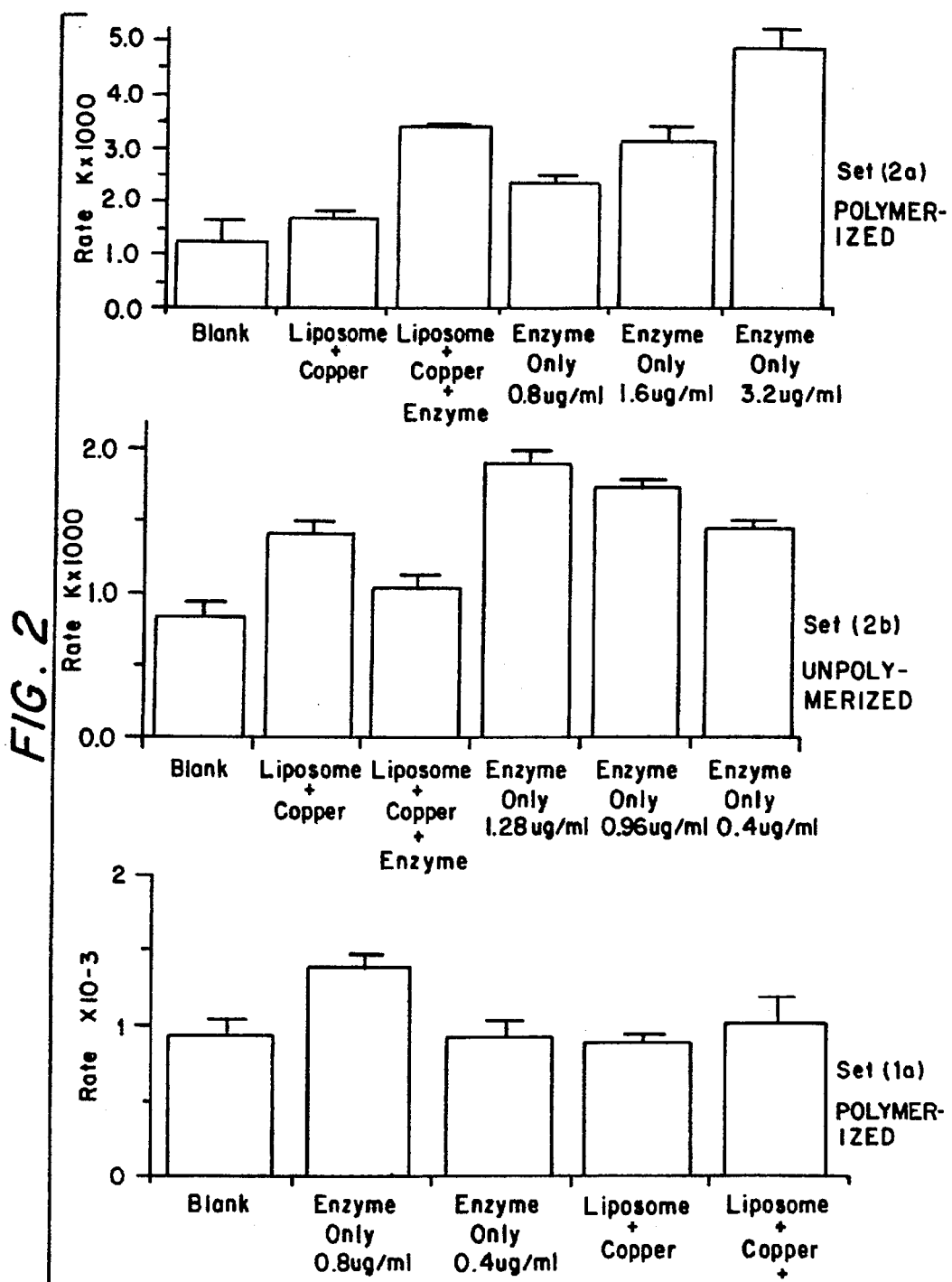
FIG. 2 is a bar graph representation of the activity of the carbonic anhydrase enzyme under various conditions of immobilization as compared to a blank and standard concentrations of the enzyme.

In SET (2b) of FIG. 2 wherein lipids (8f) and (13) were NOT polymerized (i.e. in contrast to SET (2A)), the RELATIVE activity of the carbonic anhydrase attached to the unpolymerized lipids (8f) (i.e. only lipids (8f) contain an IDA moiety capable of immobilizing the enzyme via the $Cu^{+2}$ bridge) is less than the activity of the enzyme alone (at 0.96 µg/ml concentration of enzyme alone) as measured by the reaction rate determined by the enzyme assay described above. Lipids (8f) capable of chelating with the carbonic anhydrase via the chelated copper ions break free from the non-polymerized liposomes formed in SET (2b) resulting in a relatively lowered carbonic anhydrase activity as measured by the reaction rate determined by the enzyme assay described above.

In SET (1a) of FIG. 2 wherein lipids (8e) and (13) were polymerized, the RELATIVE activity of the carbonic anhydrase attached to lipids (8e) (i.e. only lipids (8e) contain an IDA moiety capable of immobilizing the enzyme via the $Cu^{+2}$ bridge) is less than the activity of the enzyme alone (at 0.8 µg/ml concentration of enzyme alone) as measured by the reaction rate determined by the enzyme assay described above. Lipids (8e) capable of chelating the carbonic anhydrase via the chelated copper ions break free from the polymerized liposomes formed in SET (1a). The lipids (8e) break free from the polymerized liposomes of SET (1a) because only lipids (13) contain the unsaturation necessary for lipids (13) to polymerize. Since lipids (8e) do not contain any unsaturation wherein R=R'=—$(CH_2)_{14}$—$CH_3$, the liposomes of SET (1a) are incapable of polymerizing the metal chelating lipids (8e) with the polymerizable lipids (13).

The inability of lipids (8e) to polymerize is reflected by the relatively lower activity of the carbonic anhydrase (i.e. the carbonic anhydrase attached to lipids (8e) via the chelated $Cu^{+2}$ ions) in comparison to the activity of the enzyme alone (at 0.8 µg/ml concentration of enzyme alone) as measured by the reaction rate determined by the enzyme assay described above.

In contrast, the carbonic anhydrase enzyme immobilized via the $Cu^{+2}$ ions chelated to the polymerized lipids (8f) of SET (2a) is IMMOBILIZED onto the surface of the liposome due to the polymerization of lipids (8f) to other lipids (8f) and/or lipids (13). Thus, as expected, the RELATIVE carbonic anhydrase activity is greater for the liposomes of SET (2a) than that of the enzyme alone (at 0.8 µg/ml concentration of enzyme alone) as measured by the reaction rate determined by the enzyme assay described above.

The ability to immobilize the proteins or enzymes onto the liposomes formed is due to the ability of the metal chelating lipids to polymerize with other metal chelating lipids and with other non-chelating lipids that make up the liposomes. In the examples discussed above, the ability to chelate is attributed to the presence of an IDA metal chelating moiety in the head group of the metal chelating lipids and the presence of —$N^+(CH_3)_3$ in the head group of the non-chelating lipids.

What is claimed is:

1. A phospholipid having the formula:

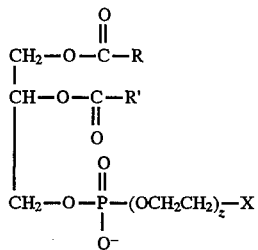

(a) wherein R and R' are organic groups;
(b) wherein at least one of R and R' is selected from the group consisting of an unsaturated alkyl group, an unsaturated acid or an unsaturated ester;
(c) wherein X is a group having a terminal iminodiacetic acid moiety; and
(d) wherein z is an integer from 1–20 including 1 and 20.

2. The phospholipid of claim 1
(a) wherein at least one of R and R' is selected from the group consisting of

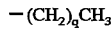

and

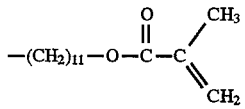

and

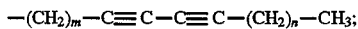

(b) wherein R and R' may be the same or different;
(c) wherein at least one of R and R' is unsaturated;
(d) wherein X is selected from the group consisting of

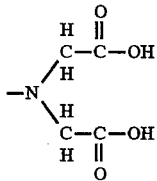

and

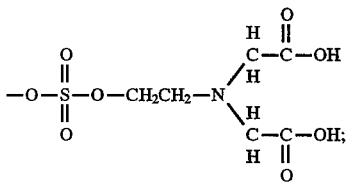

(e) wherein n, m, and q are integers;
(f) wherein n is an integer from 1 to 27, inclusive;
(g) wherein m is an integer from 2 to 28, inclusive;
(h) wherein $3 \leq (n+m) \leq 29$; and
(i) wherein q is an integer from 1 to 20, inclusive.

3. The phospholipid of claim 2,
(a) wherein $10 \leq (n+m) \leq 29$;
(b) wherein q is an integer from 5 to 18, inclusive; and
(c) wherein z is an integer from 1 to 15, inclusive.

4. The phospholipid of claim 3,
(a) wherein $15 \leq (n+m) \leq 29$;
(b) wherein q is an integer from 10 to 17, inclusive; and
(c) wherein z is an integer from 1 to 10, inclusive.

5. The phospholipid of claim 4,
(a) wherein $20 \leq (n+m) \leq 29$;
(b) wherein q is an integer from 11 to 16, inclusive; and
(c) wherein z is an integer from 1 to 5, inclusive.

6. The phospholipid of claim 4,
(a) wherein $21 \leq (n+m) \leq 27$;
(b) wherein q is an integer from 12 to 16, inclusive; and
(c) wherein z is an integer from 1 to 3, inclusive.

7. The phospholipid of claim 1,
(a) wherein R and R' are selected from the group consisting of an unsaturated alkyl group, an unsaturated acid or an unsaturated ester.

8. The phospholipid of claim 2,
(a) wherein R and R' are selected from the group consisting of

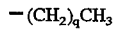

and

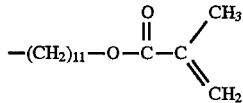

and

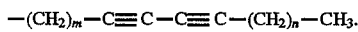

9. The phospholipid of claim 8,
(a) wherein $10 \leq (n+m) \leq 29$;
(b) wherein q is an integer from 5 to 18, inclusive; and
(c) wherein z is an integer from 1 to 15, inclusive.

10. The phospholipid of claim 9,
(a) wherein $15 \leq (n+m) \leq 29$;
(b) wherein q is an integer from 10 to 17, inclusive; and
(c) wherein z is an integer from 1 to 10, inclusive.

11. The phospholipid of claim 10,
(a) wherein $20 \leq (n+m) \leq 29$;
(b) wherein q is an integer from 11 to 16, inclusive; and
(c) wherein z is an integer from 1 to 5, inclusive.

12. The phospholipid of claim 11,
(a) wherein $21 \leq (n+m) \leq 27$;
(b) wherein q is an integer from 12 to 16, inclusive; and
(c) wherein z is an integer from 1 to 3, inclusive.

* * * * *